US00PP18475P2

(12) United States Plant Patent
Korlipara

(10) Patent No.: US PP18,475 P2
(45) Date of Patent: Feb. 5, 2008

(54) ***COREOPSIS* PLANT NAMED 'RP #5'**

(50) Latin Name: ***Coreopsis* hybrid**
Varietal Denomination: RP #5

(75) Inventor: Harini Korlipara, Canby, OR (US)

(73) Assignees: The Ivy Farm, Locustville, VA (US); Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/592,053

(22) Filed: Nov. 1, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP15,455 P3 * 12/2004 Faria ..... Plt./263

* cited by examiner

*Primary Examiner*—Wendy Haas
(74) *Attorney, Agent, or Firm*—Klarquist Sparkman, LLP

(57) ABSTRACT

A new and distinct *Coreopsis* plant named 'RP #5' characterized by very free flowering rust orange colored, daisy-like flowers, a low mounding habit, and excellent vigor.

1 Drawing Sheet

Figure 1:
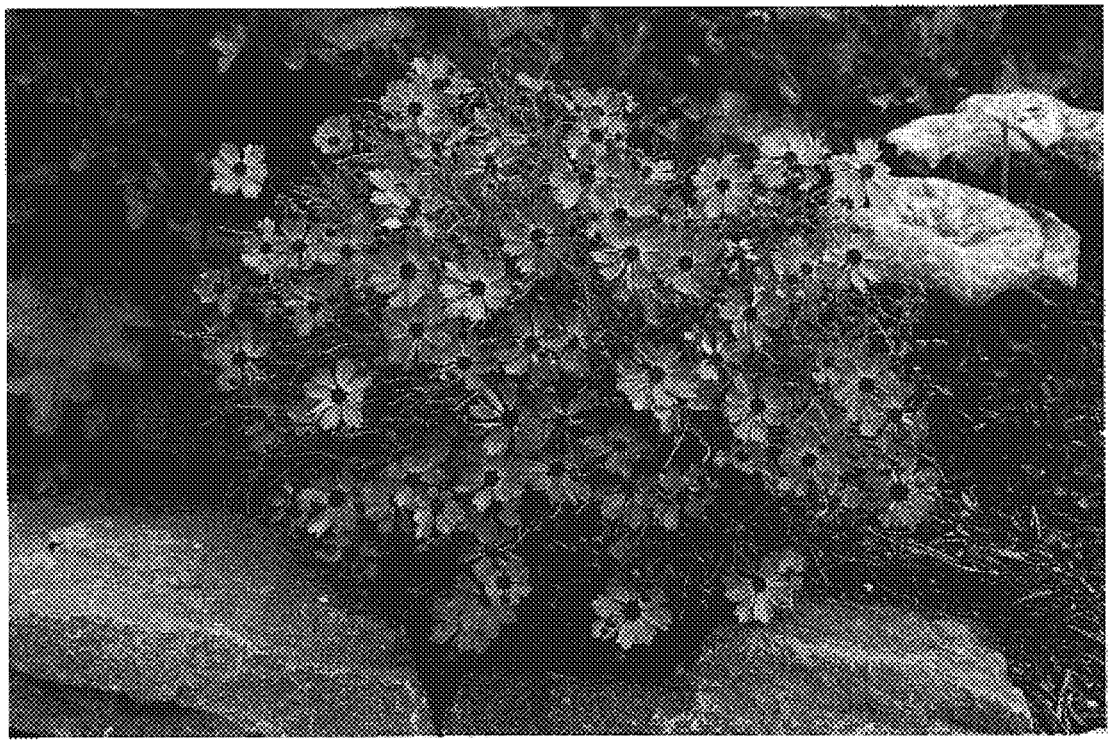

Botanical designation: *Coreopsis* hybrid (of unknown origin).
Variety denomination: 'RP #5'.

CROSS REFERENCE TO RELATED APPLICATIONS

The present application is related to U.S. Plant patent application Ser. No. 11/488,815, directed to a *Coreopsis* plant named 'Rum Punch'; U.S. Plant patent application Ser. No. 11/592,654, directed to a *Coreopsis* plant named 'RP #1'; and to U.S. Plant patent application Ser. No. 11/592,083, directed to a *Coreopsis* plant named 'RP#4'.

BACKGROUND OF THE INVENTION

The present invention relates to a new and distinct plant of *Coreopsis* and given the cultivar name 'RP #5'. *Coreopsis* is in the family Asteraceae. This new cultivar originated as a tissue culture mutation from *Coreopsis* 'Rum Punch' (U.S. Plant patent application Ser. No. 11/488,815). 'RP #5' was one of several interesting mutations.

SUMMARY OF THE INVENTION

The following traits have been repeatedly observed and are determined to be the unique characteristics of 'RP #5'. These characteristics in combination distinguish 'RP #5' as a new and distinct cultivar:

1. Unique rust orange colored daisy-like flowers.
2. Low, mounding habit.
3. Very free flowering.
4. Excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

FIG. 1 shows a one year old *Coreopsis* 'RP #5' growing in the ground in the garden in full sun in August in Canby, Oreg.

DETAILED PLANT DESCRIPTION

The following is a detailed description of the new *Coreopsis* cultivar based on observations of a one-year-old specimen grown in the ground in full sun under typical outdoor conditions in the trial fields in August in Canby, Oreg.. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Type.*—Herbaceous perennial, grown as an annual.
*Hardiness.*—USDA Zone 9–10.
*Size.*—45 cm wide and 28 cm tall to top of flowers.
*Form.*—Low mound with freely branching stems.
*Vigor.*—Excellent.
*Roots.*—Fibrous, freely branching, fine, Yellow White 158A; roots develop easily from stem cuttings.

Stem:

*Type.*—Ascending.
*Size.*—28 cm tall and 1 to 4 mm wide.
*Internode length.*—1.5 to 5.5 cm.
*Surface.*—Glabrous.
*Color.*—Green 147B.

Leaf:

*Type.*—Simple.

*Shape.*—Mostly linear (sometimes oblanceolate) with some basal leaves with one to two linear side lobes near base of the leaf.

*Arrangement.*—Opposite.

*Size.*—Grows to 6.3 cm long and 3.5 mm wide when linear, side lobe(s) from near base of leaf, grow to 21 mm long and 1 mm wide.

*Margins.*—Entire.

*Apex.*—Acute.

*Base.*—Clasping.

*Surface texture.*—Glabrous on both sides.

*Venation.*—Pinnate.

*Color.*—Top side — Green 147A. Bottom — Green 148B.

Immature inflorescence: Globular, 4 mm wide and 4 mm deep, Greyed Orange 175A on tip and seams with Greyed Orange 163B in the middle and the bottom Green 137A.

Inflorescence:

*Type.*—Long stalked terminal heads of daisy type flowers.

*Peduncle.*—Grows to 7.5 cm tall and 0.5 mm wide, glabrous, Green 137A.

*Size.*—3.3 cm wide and 8 mm deep.

*Ray florets.*—8 in number, no pistil or stamen, obovate, the tip three with the terminal lobe the longest, margins entire, base cuneate, grows to 17 mm long and 9 mm wide, glabrous on both surfaces, 2 mm claw at base, laminae sometimes with one linear appendage on side or opposite and upright, grows to 9 mm long. Color: Ray floret, topside — most Greyed Orange 167A darkening toward the tips to Greyed Orange 171A, some Greyed Orange 171A darkening toward the tips to Greyed Red 178B; Yellow 12A at the base and claw. Ray floret, bottom side — Greyed Orange 167C with Greyed Red 178 near top.

*Cone.*—Conic in shape, grows to 6 mm wide and 3 mm deep, Greyed Purple 187A.

*Disc florets.*—Corolla — 3 mm long and less than 1 mm wide, tubular, 4 lobed, Greyed Purple 187A on the lobes to Yellow Orange 15A on tube inside and out, glabrous. Pistil — 5 mm long, 2-branched stigma extruding from the corolla, style 3.5 mm long, Orange 17A overall, ovary 1.5 mm long, White 155A. Stamen — 4, filaments 3 mm long, extruding, Black 202A, pollen Orange 17A.

*Phyllaries.*—In 2 series, series closest to ray florets 8 in number, ovate, entire, acute, in an area 6 mm deep and 10 mm wide, glabrous, Orange 28B on top half with edges Greyed Purple 187A, and Yellow Green 147B on bottom half; lower series 5 to 6 in number, each lobe 3 mm long and 1 mm wide at the base, ovate, entire, acute, glabrous, Yellow Green 147A.

*Bloom period.*—June through September in Canby, Oreg.

*Fragrance.*—Light, daisy like.

Seed: None produced.

*Fertility.*—Infertile.

Disease and pests: *Coreopsis* are susceptible to mildew and fungal spots. No known resistances on the new cultivar.

COMPARISONS TO SIMILAR *COREOPSIS*

Compared to *Coreopsis* 'Limerock Ruby' (U.S. Plant Pat. No. 15,455), this new cultivar has a new and unique flower color of rust orange rather than rose pink.

Compared to *Coreopsis* 'Rum Punch' (U.S. Plant patent application Ser. No. 11/488,815), the new cultivar has flowers of a rust orange color rather than orangey rose.

Compared to *Coreopsis* 'RP #4' (U.S. Plant patent application Ser. No. 11/152,083), *Coreopsis* 'RP #5' has flowers of rust orange rather than rusty-yellow.

I claim:

1. A new and distinct *Coreopsis* plant as herein illustrated and described.

* * * * *

UNITED STATES PATENT AND TRADEMARK OFFICE

CERTIFICATE OF CORRECTION

PATENT NO. : PP 18,475 P2
APPLICATION NO. : 11/592053
DATED : February 5, 2008
INVENTOR(S) : Harini Korlipara It is certified that error appears in the above-identified patent and that said Letters Patent is hereby corrected as shown below:

Column 4, line 35, "11/152,083" should be --11/592,083--.

Signed and Sealed this

Twenty-ninth Day of July, 2008

JON W. DUDAS
*Director of the United States Patent and Trademark Office*